United States Patent
Jeffrey et al.

(10) Patent No.: US 7,037,281 B1
(45) Date of Patent: May 2, 2006

(54) ARM SLING APPARATUS

(76) Inventors: M. Neil Jeffrey, 415 Southwood Dr., Wabash, IN (US) 46992; Esther M. Daht, 21052 Amberwick La., Huntington Beach, CA (US) 92646

( * ) Notice: Subject to any disclaimer, the term of this patent is extended or adjusted under 35 U.S.C. 154(b) by 0 days.

(21) Appl. No.: 11/170,563

(22) Filed: Jun. 29, 2005

(51) Int. Cl.
*A61F 5/00* (2006.01)

(52) U.S. Cl. .............................. 602/4; 602/20
(58) Field of Classification Search .............. 602/4, 602/20, 60, 5; 2/44, 45
See application file for complete search history.

(56) References Cited

U.S. PATENT DOCUMENTS

| | | | | |
|---|---|---|---|---|
| 2,560,243 A | * | 7/1951 | Peterson | 602/4 |
| 3,559,640 A | * | 2/1971 | Beckett | 602/4 |
| 4,071,022 A | * | 1/1978 | Ewers | 602/4 |
| 4,526,164 A | * | 7/1985 | Bihl | 602/4 |
| 4,901,713 A | * | 2/1990 | Troeger | 602/4 |
| 5,141,488 A | | 8/1992 | Schrader | |
| 5,395,306 A | * | 3/1995 | Bauerfeind et al. | 602/61 |
| 5,413,552 A | | 5/1995 | Iwuala | |
| 5,820,572 A | * | 10/1998 | Palmer | 601/41 |
| 5,823,851 A | * | 10/1998 | Dicker | 450/2 |
| 6,302,761 B1 | * | 10/2001 | Wrenn | 450/86 |
| 6,361,478 B1 | * | 3/2002 | Giancaspro | 482/69 |
| 6,387,067 B1 | * | 5/2002 | Hebert | 602/20 |
| 6,406,449 B1 | * | 6/2002 | Moore et al. | 602/4 |
| 6,440,094 B1 | * | 8/2002 | Maas | 602/5 |
| 6,685,662 B1 | * | 2/2004 | Curry et al. | 602/20 |
| 6,709,411 B1 | * | 3/2004 | Olinger | 602/4 |

* cited by examiner

*Primary Examiner*—Kim M. Lewis
(74) *Attorney, Agent, or Firm*—Frank D. Lachenmaier

(57) ABSTRACT

This invention relates generally to a unique arm support device in which the shoulder straps are designed to evenly distribute the weight of the person's arm evenly across both shoulders and not put a side or forward stress on the wearer's neck. This device also allows a patient, such as a stroke victim who has the use of only one arm and hand, to put this sling on and remove it without assistance.

3 Claims, 4 Drawing Sheets

ARM SLING APPARATUS

BACKGROUND

1. Field of Invention

This invention relates generally to a unique arm support device in which the shoulder straps are designed to evenly distribute the weight of the person's arm evenly across both shoulders and not put a side load on the wearer's neck. This device also allows a patient, such as a stroke victim who has the use of only one arm and hand, to put this sling on and remove it without assistance and it works equally well for a right or left arm injury.

2. Prior Art

Prior art in the field of arm support includes many different forms of slings. Most of these slings do not distribute the weight of the arm and sometimes a cast equally on both shoulders. Typically they have a strap over the opposite shoulder from the injured or inoperative arm. These single strap devices tend to place an unwanted pressure against the side of the neck. For many wheel chair bound stroke patients with the need to wear a sling during all their waking hours, the standard sling can cause the head to be pulled over and down exacerbating their original problem.

There are several devices that have tried to solve this problem, one of which is described in U.S. Pat. No. 5,413,552 Iwuala 1995 wherein a sling with Humeral Stabilizer is disclosed. All though this device claims to have eliminated the side load to the neck it is a fairly complex mechanism with two straps, multiple strap fasteners and adjusters and fastens to a torso belt. The most significant problem with these type support devices is that they would be very difficult if not impossible for a person with the use of only one hand to put on or take off without assistance and will be relatively expensive to manufacture.

The second patented device that attempts to solve this problem is described in U.S. Pat. No. 5,141,488 Schrader 1992 wherein a basic pair of suspenders, crossed in the back and clipped on the waist band of a skirt or pair of slacks in both the front and back have adjustable length loops secured to the front of each strap. One adjustable length loop supports the hand or wrist of a patient while the second supports the lower arm. Again this device would be virtually impossible for a person with the use of only one arm to put on or take off with out assistance.

SUMMARY

An object of the present invention is to provide Arm Sling Apparatus for supporting an injured or inoperable arm for long periods of time without forward or sideways stress on the wearer's neck.

Another object of the present invention is to provide Arm Sling Apparatus for supporting an injured or inoperable arm that has no adjustable straps or fasteners and could be put on or taken off by the patient without assistance.

A further object is to provide Arm Sling Apparatus for supporting an injured or inoperable arm that is simple and inexpensive to manufacture.

A further object is to provide an Arm Sling Apparatus for supporting an injured or inoperable arm that is self sustaining and does not attach to the waistband of a skirt or slacks since some patients do not dress in such a manner all of the time.

DRAWINGS

In order that Sling may be more fully understood it will now be described by way of example, with reference to the accompanying exemplary drawings in which.

REFERENCE NUMERALS

Figure 1:
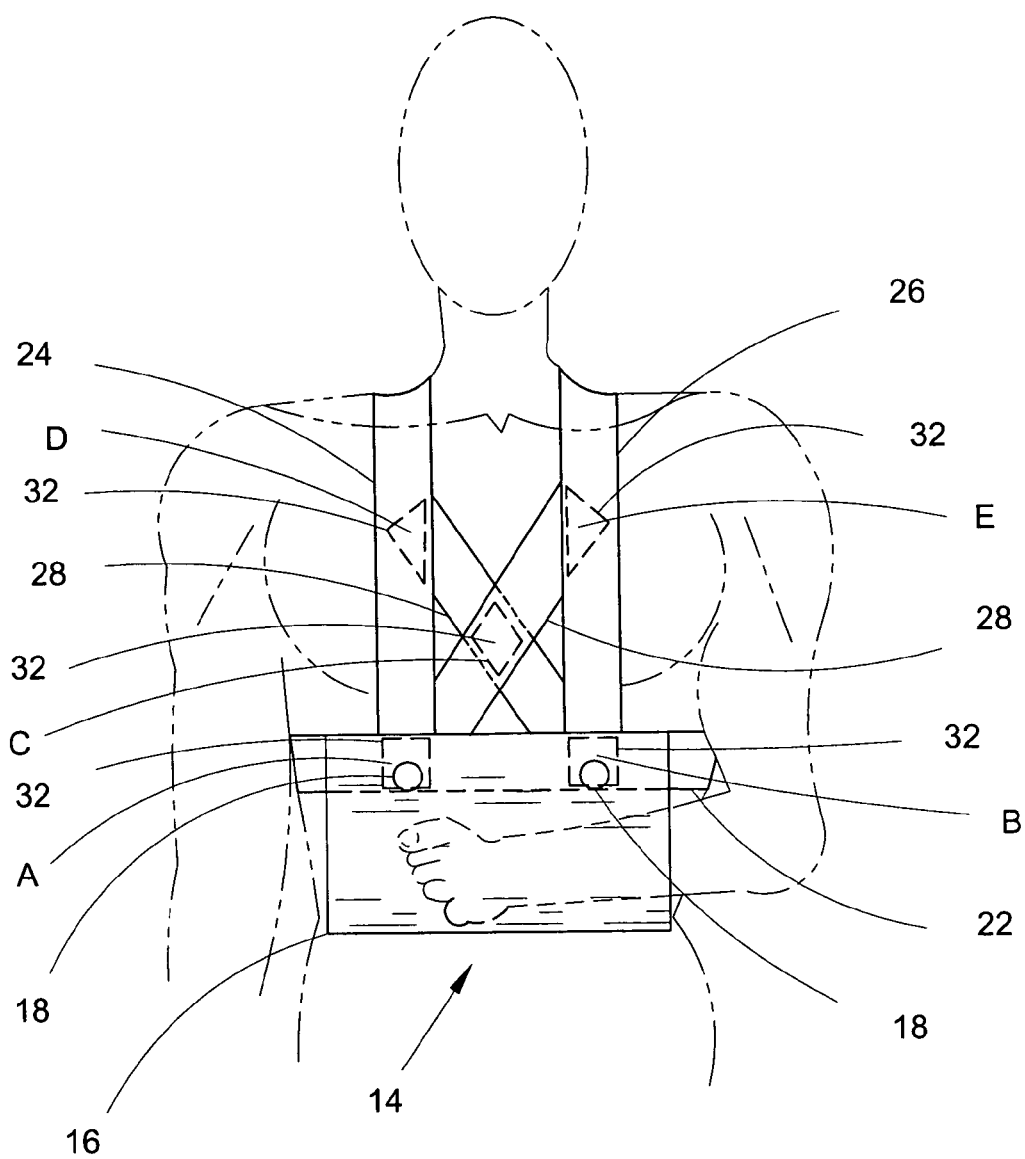
FIG. 1 is a front view of an Arm Sling Apparatus supporting a patient's left arm.

The same reference numbers are used to refer to the same or similar parts.

| | |
|---|---|
| 14 | Arm Sling Apparatus |
| 16 | sleeve |
| 18 | buttons |
| 20 | Velcro |
| 22 | waist band |
| 24 | right shoulder strap |
| 26 | left shoulder strap |
| 28 | front cross strap |
| 30 | rear cross strap |
| 32 | strap stitching |

A—right shoulder strap to front of waist band
B—left shoulder strap to front of waistband
C—cross over point of front cross straps
D—front cross strap to front of right shoulder strap
E—front cross strap to front of left shoulder strap
F—left shoulder strap to rear of waistband
G—right shoulder strap to rear of waist band
H—cross over of rear cross straps
J—rear cross strap to rear of left shoulder strap
K—rear cross strap to rear of right shoulder strap

DESCRIPTION

The present invention, in its several embodiments, meets the above mentioned objectives.

An object of the present invention is to provide a sling device for supporting an injured or inoperable arm for long periods of time without forward or sideways stress on the wearer's neck. This is accomplished by fastening two elastic shoulder straps to an elastic waist band with front and back cross straps of the same elastic material, keeping the shoulder straps from sliding off the shoulders and a pouch for supporting an injured or inoperative arm formed of a soft fabric material attached to the waist band on the back of the pouch and buttoned or fastened with Velcro or the like on the top front of the pouch.

Another object of the present invention is to provide a sling device for supporting an injured or inoperable arm that has no adjustable straps or fasteners and could be put on or taken off by the patient without assistance. In the preferred embodiment the elastic waistband is approximately 2 inches smaller than the waist of the patient. Several different sizes for different size patients can be readily envisioned by someone skilled in this art. The elastic shoulder straps are also the approximate distance from the waist band, over the shoulder and back to the waistband again less approximately two inches. The patient is able to place the waistband over his arms and head and pull it into position with his good hand, lay his injured arm on the open sleeve and fasten the top, completing the sleeve pouch.

A further object is to provide a sling device for supporting an injured or inoperable arm that is simple and inexpensive to manufacture. In the preferred embodiment of this invention the support harness is fabricated from 2 inch wide elastic material such as Stretchrite Elastic from Rode Island Textile Co., Pawtucket, R.I. 02862. The pouch can be fabricated from a rectangular sheet of fabric and attached to the waistband with either two buttons sewn on the front of the waistband engaging the top back surface of the pouch or strips of Velcro type hook and eyes. Seven appropriate lengths of elastic strapping, one 12 by 24 sheet of fabric and two fasteners simply assembled makes the manufacture of the present invention very inexpensive compared to the prior art systems with all the numerous attachment and adjustment features. There are no clips, clamps or strap adjustments to be made with elastic strapping compensating for some variations in patient size. Several different size apparatus can cover the range of patient sizes. The system is simple enough that it can be supplied in kit form and custom fit to a patient with simple sewing assembly steps.

A further object is to provide a sling device for supporting an injured or inoperable arm that is self sustaining and does not attach to the waistband of a skirt or slacks since some patients do not dress in such a manner all of the time. In the present invention the shoulder straps are sewn to the elastic waistband and the pouch is also attached to the elastic waistband with no attachment to clothing required.

DETAILED DESCRIPTION OF THE PREFERRED EMBODIMENTS

FIG. 1 shows a front view of an Arm Sling Apparatus 14 on a patient's left arm. For the preferred embodiment there is an elastic waistband 22 with an approximately 2 inches smaller circumference than the waist of the patient. There is a right shoulder strap 24 and a left shoulder strap 26 sewn to the inside of waistband 22 in the front at points A and B respectively. These straps are approximately two inches less than the length of the distance from the upper waist of the patient, over the shoulder and back to the waistband. There are two front cross straps 28 that are also sewn into the waistband 22 at points A and B and are sewn into the opposite shoulder strap at approximately points C and D. The two cross straps 30 are sewn together where they cross at point E. An approximate 13 inch wide by 28 inch long rectangle of fabric which makes sleeve 16 is sewn onto the front of the center of waistband 22 or attached removably with buttons 18 which have been sewn on the front of waistband 22 at points A and B. At the bottom of sleeve fabric, two button holes are placed in the fabric matching the locations of buttons 18 when the fabric is pulled up and buttoned forming the sling pouch 16.

Figure 2:
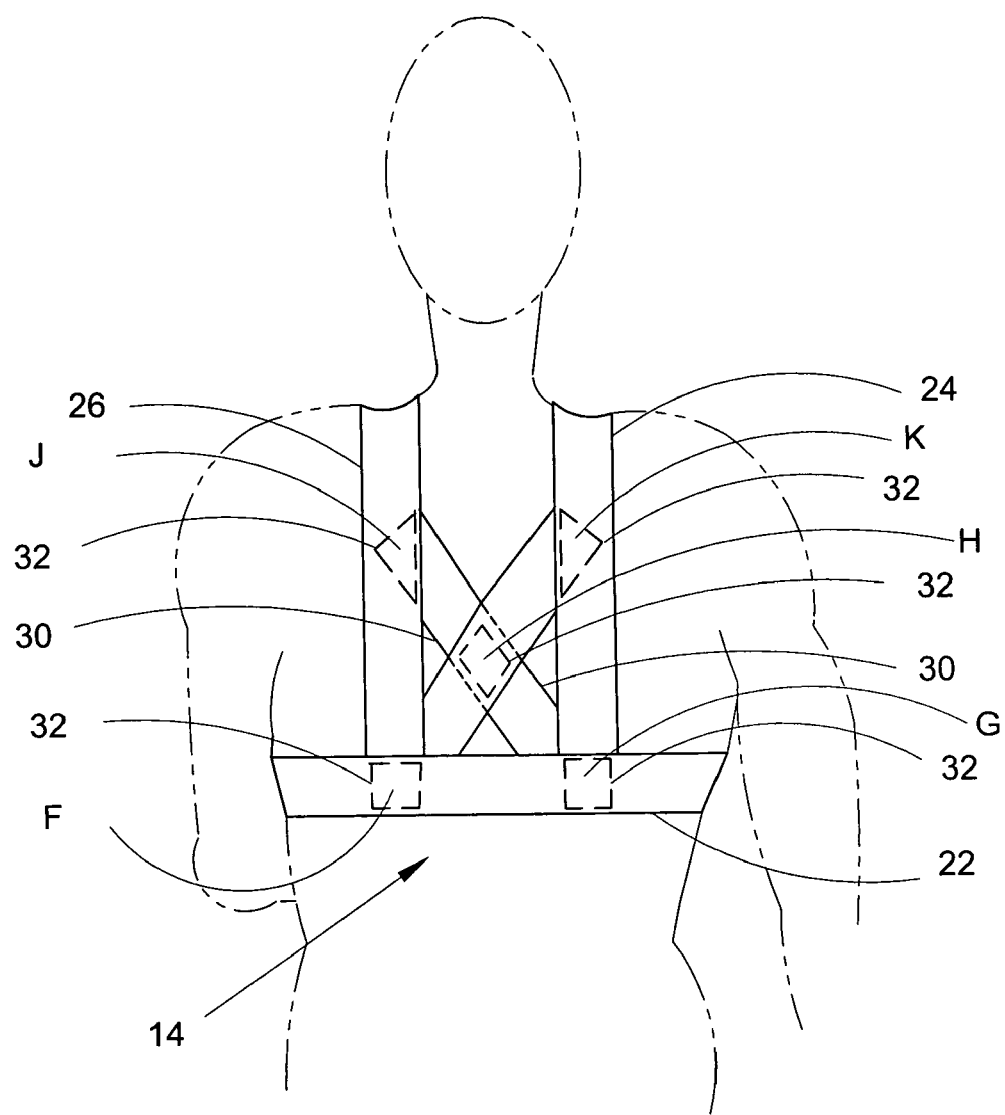
FIG. 2 is a rear view of the same Arm Sling Apparatus on said patient.

FIG. 2 shows a rear view of a patient wearing Arm Sling Apparatus 14. In the preferred embodiment of Arm Sling Apparatus 14 there are also rear cross straps 30 on the back of Arm Sling Apparatus 14 attached again where the shoulder straps 24 and 26 attach to waistband 22 at points F and G respectively and to the opposite shoulder strap at points K and J. These also are sewn together where they cross at point H.

Figure 3:
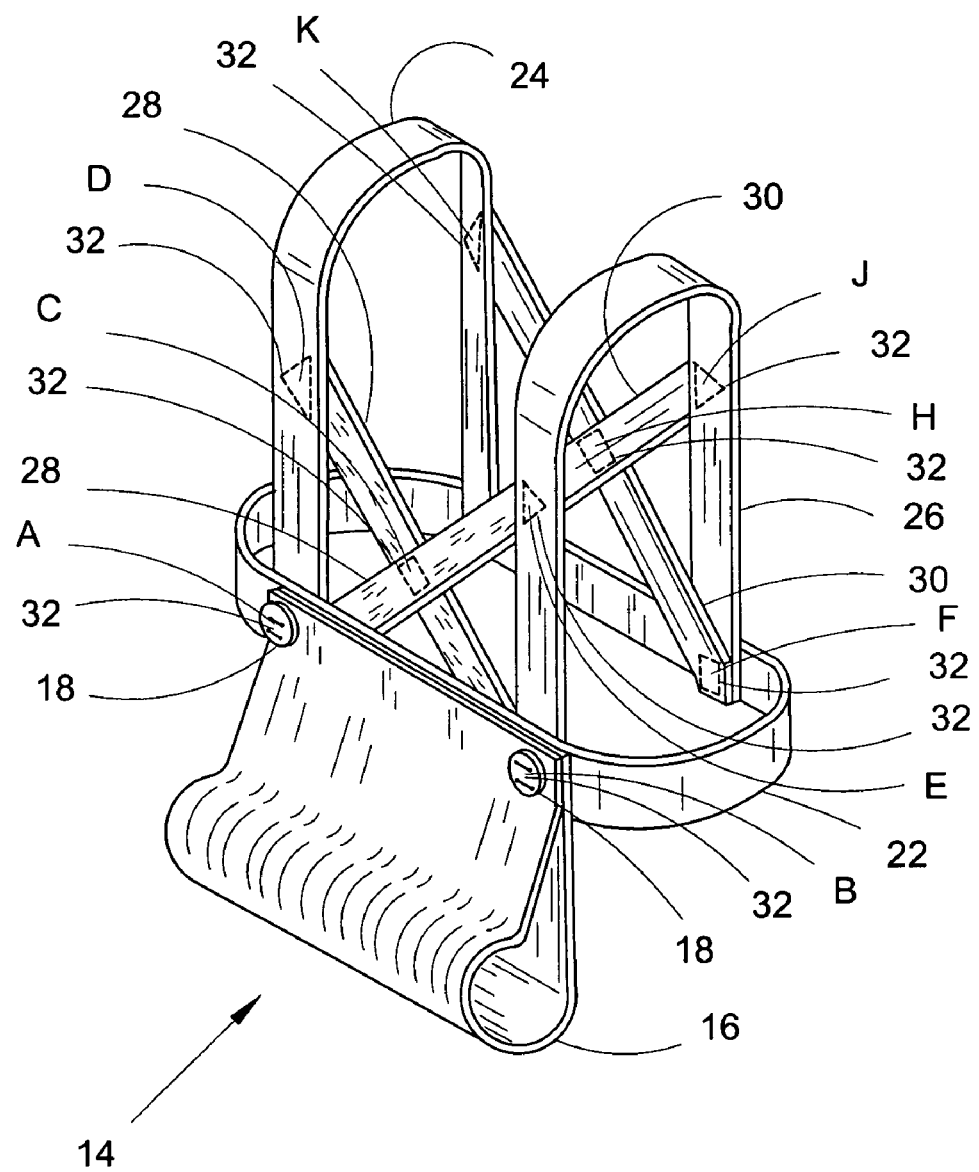
FIG. 3 is a perspective view of an Arm Sling Apparatus.
Figure 3A:
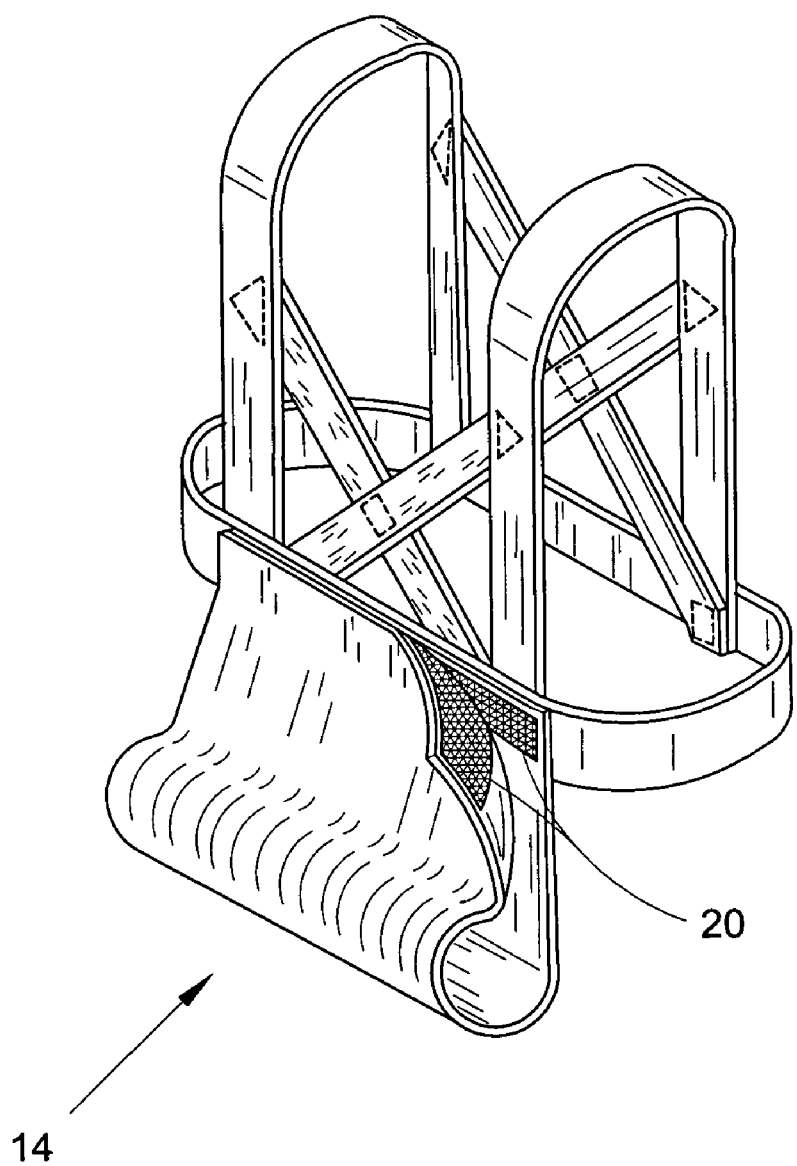
FIG. 3A is a perspective view of a second embodiment of an Arm Sling Apparatus.

FIG. 3 shows a perspective view of Arm Sling Apparatus 14 without the patient and the fabric rectangle folded up and buttoned at the top, forming sleeve 16.

OPERATION OF THE PREFERRED EMBODIMENTS

An Arm Sling Apparatus 14 apparatus is placed over a patients head and waistband 22 is pulled down to place a small tension on shoulder straps 24 and 26. The patient's injured arm is placed on the rectangle of sleeve 16 fabric which has been attached at the top to waistband 22 by buttons 18. The bottom of the fabric is then lifted up and buttoned using the two buttons 18 attached to the front of waistband 22, forming a pouch or sleeve 16 that supports the injured arm. The sleeve can be removed from the elastic harness for separate laundering if desired.

The description of the Arm Sling Apparatus 14 above is not intended to limit this invention to a particular size apparatus or the techniques of attaching the straps or sleeve to the waistband and each other. Scaling in both size and material selection to suit these purposes can be easily understood by someone of ordinary skill in these arts. Although the preferred embodiment is described with buttons 18, it is not so limited and several other fastening techniques for the top of the sleeve fabric could be selected from other techniques familiar to those of ordinary skill in these fabrication arts such as snaps, hook and eye or a Velcro type of hook and loop.

What is claimed is:

1. An Arm Sling apparatus for supporting an injured or inoperative arm which does not place a side or forward force on the neck of a patient comprising:
    a) a waistband of generally circular shape with a front and a back side, adapted to be worn around the patient's upper waist made from an elastic material;
    b) a right shoulder strap and a left shoulder strap affixed to said waistband on the said front side and stretched over the apex of said shoulder and affixed to said back side of said waistband made from an elastic material;
    c) front and back cross straps made from an elastic material affixed to said waistband at the same point as said right and left shoulder straps and crossing over each other and affixing to opposite shoulder strap at a point midway to the apex of said shoulder strap and said cross straps being secured to each other at the points where they cross whereby said shoulder straps are prevented from sliding off said shoulders;
    d) a sleeve adapted to support said injured arm made from a rectangle of fabric with a top and a bottom where said top is affixed to said waistband and said bottom of said rectangle is lifted to level of said waistband and removably attached to said waistband forming said sleeve with openings from both the left and the right whereby said arm sling apparatus can be used for either arm and making it possible for a patient with the use of only one hand to install sleeve over inoperative arm.

2. The apparatus of claim 1 wherein said sleeve bottom's removable attachment means are selected from a group comprising: buttons on said top of fabric rectangle and button holes on said bottom of fabric rectangle, hooks on said top and eyes on said bottom of fabric rectangle, loop strip on said top of said fabric rectangle and hook strip on said bottom of fabric rectangle.

3. The apparatus of claim 1 wherein said sleeve top is affixed by a removable means consisting of button holes in said top of said fabric rectangle and buttons sewn on said front of said waistband; and a permanent means of sewing said top of said fabric rectangle to said front of said waistband.

* * * * *